US012561873B2

(12) United States Patent
Wahrenberg

(10) Patent No.: US 12,561,873 B2
(45) Date of Patent: Feb. 24, 2026

(54) IMAGE PROCESSING APPARATUS AND METHOD

(71) Applicant: CANON MEDICAL SYSTEMS CORPORATION, Otawara (JP)

(72) Inventor: Magnus Fredrik Wahrenberg, Edinburgh (GB)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 449 days.

(21) Appl. No.: 18/171,522

(22) Filed: Feb. 20, 2023

(65) Prior Publication Data
US 2024/0282021 A1 Aug. 22, 2024

(51) Int. Cl.
*G06T 11/00* (2006.01)
*A61B 6/42* (2024.01)
(Continued)

(52) U.S. Cl.
CPC .......... *G06T 11/008* (2013.01); *A61B 6/4241* (2013.01); *G06T 15/08* (2013.01);
(Continued)

(58) Field of Classification Search
CPC ... G06T 2207/10072–10128; G06T 2211/408; G06T 11/008; G06T 2210/41;
(Continued)

(56) References Cited

U.S. PATENT DOCUMENTS 6,246,784 B1 6/2001 Summers et al.
2007/0097143 A1 5/2007 Ii et al.
(Continued)

FOREIGN PATENT DOCUMENTS

CN 111260632 A 6/2020
CN 114334094 A 4/2022
(Continued)

OTHER PUBLICATIONS

Ikits, M., et al., Chapter 39. Volume Rendering Techniques [online], 2022 [retrieved on Jul. 2, 2025], NVIDIA, Retrieved from the Internet: <https://web.archive.org/web/20221005155557/https://developer.nvidia.com/gpugems/gpugems/part-vi-beyond-triangles/chapter-39-volume-rendering-techniques> (Year: 2022).*
(Continued)

*Primary Examiner* — Andrew W Bee
*Assistant Examiner* — Emma E Dryden
(74) *Attorney, Agent, or Firm* — Oblon, McClelland, Maier & Neustadt, L.L.P.

(57) ABSTRACT
A medical image processing apparatus includes processing circuitry to receive radiation image data for each of a plurality of different channels, wherein the radiation image data for all of the plurality of channels represents a same anatomical region of a same subject; and, for each of a plurality of positions represented in the radiation image data: estimate, based on data values for the position in each of the plurality of channels, material probabilities which indicate a respective probability of each of a plurality of materials existing at the position; and specify a value for at least one rendering parameter at the position based on the material probabilities.

19 Claims, 7 Drawing Sheets

(51) Int. Cl.
  *G06T 15/08* (2011.01)
  *A61B 6/00* (2006.01)
(52) U.S. Cl.
  CPC ..... *A61B 6/482* (2013.01); *G06T 2207/30008*
  (2013.01); *G06T 2207/30088* (2013.01); *G06T*
  *2210/41* (2013.01); *G06T 2211/408* (2013.01)
(58) Field of Classification Search
  CPC ..................... G06T 15/00; G06T 15/08; G06T
  7/0012–0016; G06T 2207/10064–10136;
  G06T 5/50; A61B 6/4241; A61B 6/482;
  A61B 6/5205; A61B 6/03; A61B 6/032;
  A61B 8/483; A61B 6/00; A61B 6/5235;
  G06V 2201/03–034; G01V 5/224; G01N
  2223/423
  See application file for complete search history.

(56) References Cited

U.S. PATENT DOCUMENTS

| | | | |
|---|---|---|---|
| 2009/0028398 A1* | 1/2009 | Lundstrom | G06T 19/00 |
| | | | 382/128 |
| 2011/0033099 A1* | 2/2011 | Kadomura | G06T 7/143 |
| | | | 382/131 |
| 2011/0103663 A1 | 5/2011 | Rosenbaum et al. | |
| 2011/0228997 A1 | 9/2011 | Sharp et al. | |
| 2011/0261072 A1 | 10/2011 | Kadomura et al. | |
| 2013/0308844 A1 | 11/2013 | Florent et al. | |
| 2015/0063669 A1 | 3/2015 | Wiemker et al. | |
| 2015/0213652 A1 | 7/2015 | Voigt et al. | |
| 2016/0225140 A1 | 8/2016 | Jo et al. | |

| | | | |
|---|---|---|---|
| 2016/0317035 A1* | 11/2016 | Hendriks | A61B 10/0233 |
| 2017/0061681 A1 | 3/2017 | Engel et al. | |
| 2019/0147639 A1 | 5/2019 | Sudarsky et al. | |
| 2019/0336096 A1 | 11/2019 | Itu et al. | |
| 2021/0035293 A1 | 2/2021 | Hirai et al. | |
| 2021/0192807 A1* | 6/2021 | Menser | G06T 5/70 |
| 2022/0012878 A1 | 1/2022 | Aoyama | |
| 2023/0360201 A1* | 11/2023 | Natanzon | G06T 11/008 |
| 2024/0104797 A1* | 3/2024 | Gong | G06T 11/008 |

FOREIGN PATENT DOCUMENTS

| | | | |
|---|---|---|---|
| EP | 2989609 B1 * | 10/2019 | G06T 7/11 |
| EP | 3 965 059 A1 | 3/2022 | |
| JP | 2006-187412 A | 7/2006 | |

OTHER PUBLICATIONS

Lum, E., Wilson, B., and Ma, K., High-quality lighting and efficient pre-integration for volume rendering, 2004, In Proceedings of the Sixth Joint Eurographics—IEEE TCVG conference on Visualization (VISSYM'04), Eurographics Association. (Year: 2004).*

Kniss, J. et al., "Multi-Dimensional Transfer Functions for Volume Rendering", Scientific Computing and Imaging Institute School of Computing, University of Utah, Johnson/Hansen: The Visualization Handbook, May 20, 2004, p. 181-202. (22 pages).

Stompel, A. et al., "Visualization of Multidimensional, Multivariate Volume Data Using Hardware-accelerated Non-photorealistic Rendering Techniques", 2002 (9 pages).

Karlas, A. et al., Cardiovascular Optoacoustics: From Mice to Men—A Review. Photoacoustics. 14. 2019, 10.1016/j.pacs.2019.03.001 (13 pages).

* cited by examiner

Object 1

Object 2

IMAGE PROCESSING APPARATUS AND METHOD

FIELD

Embodiments described herein relate generally to an image processing apparatus and method, for example an apparatus and method for processing multi-dimensional radiation image data.

BACKGROUND

It is known to perform volumetric medical imaging using computed tomography (CT). In traditional CT detectors, the detectors accumulate an intensity of X-rays coming in.

In recent years, photon counting detectors for CT have been developed. Instead of accumulating the intensity of X-rays, photon counting detector hardware can look at individual photons and estimate their energy. A photon counting detector may detect individual peaks from individual photon events.

The use of photon counting detectors may facilitate multi-spectral CT in which different wavelengths can be allocated to different channels, which may also be referred to as buckets or bins. Different wavelengths correspond to different energies. Individual datasets may therefore be obtained for different classes of energy.

The division of wavelengths may be made in multiple different ways. In some examples, 5 different channels may be used, where each channel includes a respective range of wavelengths. In other examples, between 3 and 8 different channels may be used.

Volumetric medical image data may comprise a three-dimensional array of voxels, where each voxel is representative of a particular position in three-dimensional space and each voxel has one or more data values. For example in the case of traditional CT data, each voxel may have an associated intensity value that is representative of the attenuation of the applied X-ray radiation provided at the location represented by the voxel. The intensity value may be referred to as an image value, gray value, gray level, voxel value or CT value. The intensity value may be measured in Hounsfield units (HU).

The general principles of volume rendering are well known. Typically, a transfer function is used to determine optical properties of a material from sampled data. For example, the transfer functions may map different intensity values to different values of color and/or opacity. A transfer function is usually a dense representation and may be edited manually.

FIG. 1 is a flow chart illustrating in overview a typical volume rendering method for CT imaging in which a single channel of intensity data is obtained and in which a transfer function is used. At stage 10, volumetric image data is received which comprises a set of voxels each having an associated intensity value. A volume represented by the volumetric data set is sampled, for example in a ray-casting process. Intensity values for samples are obtained by interpolation of intensity values for neighboring voxels. At stage 12, intensity is classified into optical properties by use of a transfer function. For example, the transfer function may map the intensity value for each sample to a respective color and opacity value. At stage 14, integration is performed. For example, color and opacity may be integrated along rays that are cast into the volume.

In photon counting CT, the volumetric image data obtained may be, for example, a 5 channel volume in which each voxel has 5 associated intensity values, one for each channel. Such a volume may have too high a dimensionality to rely on regular transfer functions. A 5 dimensional transfer function that maps values from 5 different channels onto optical properties may be difficult to store. Furthermore, it would be very challenging to develop a user interface that would allow a user to edit such a high dimensional transfer function.

It is anticipated that a typical transfer function may only be useable with 2 or at most 3 channels. Even 2 or 3 channels may require the use of sparse storage.

BRIEF DESCRIPTION OF THE DRAWINGS

Embodiments are now described, by way of non-limiting example, and are illustrated in the following figures, in which.

DETAILED DESCRIPTION

Certain embodiments provide a medical image processing apparatus comprising processing circuitry configured to: receive radiation image data for each of a plurality of different channels, wherein the radiation image data for all of the plurality of channels represents a same anatomical region of a same subject; and, for each of a plurality of positions represented in the radiation image data: estimate, based on data values for the position in each of the plurality of channels, material probabilities which indicate a respective probability of each of a plurality of materials existing at the position; and specify a value for at least one rendering parameter at the position based on the material probabilities.

Certain embodiments provide a medical image processing method comprising: receiving radiation image data for each of a plurality of different channels, wherein the radiation image data for all of the plurality of channels represents a same anatomical region of a same subject; and, for each of a plurality of positions represented in the radiation image data: estimating, based on data values for the position in each of the plurality of channels, material probabilities which indicate a respective probability of each of a plurality of materials existing at the position; and specifying a value for at least one rendering parameter at the position based on the material probabilities.

Figure 1:
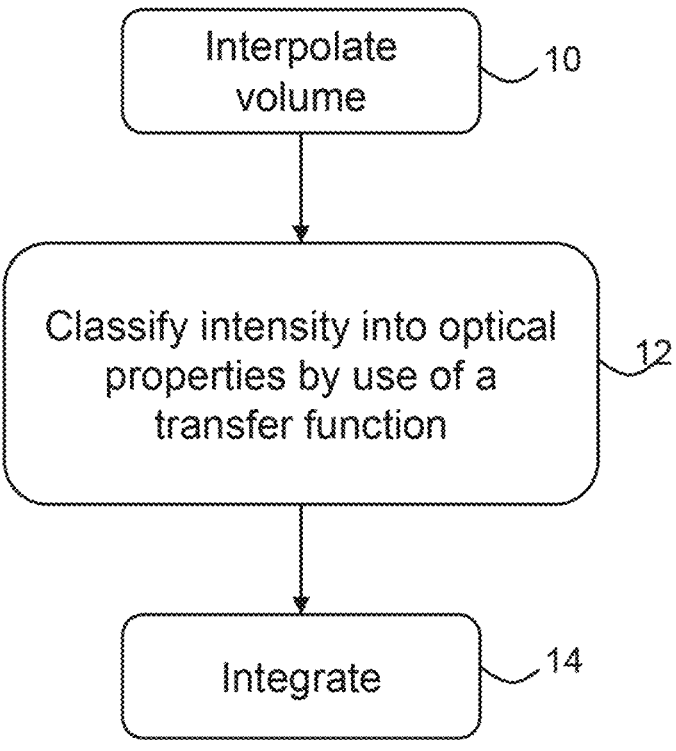
FIG. 1 is a flow chart illustrating in overview a known method of volume rendering.
Figure 2:
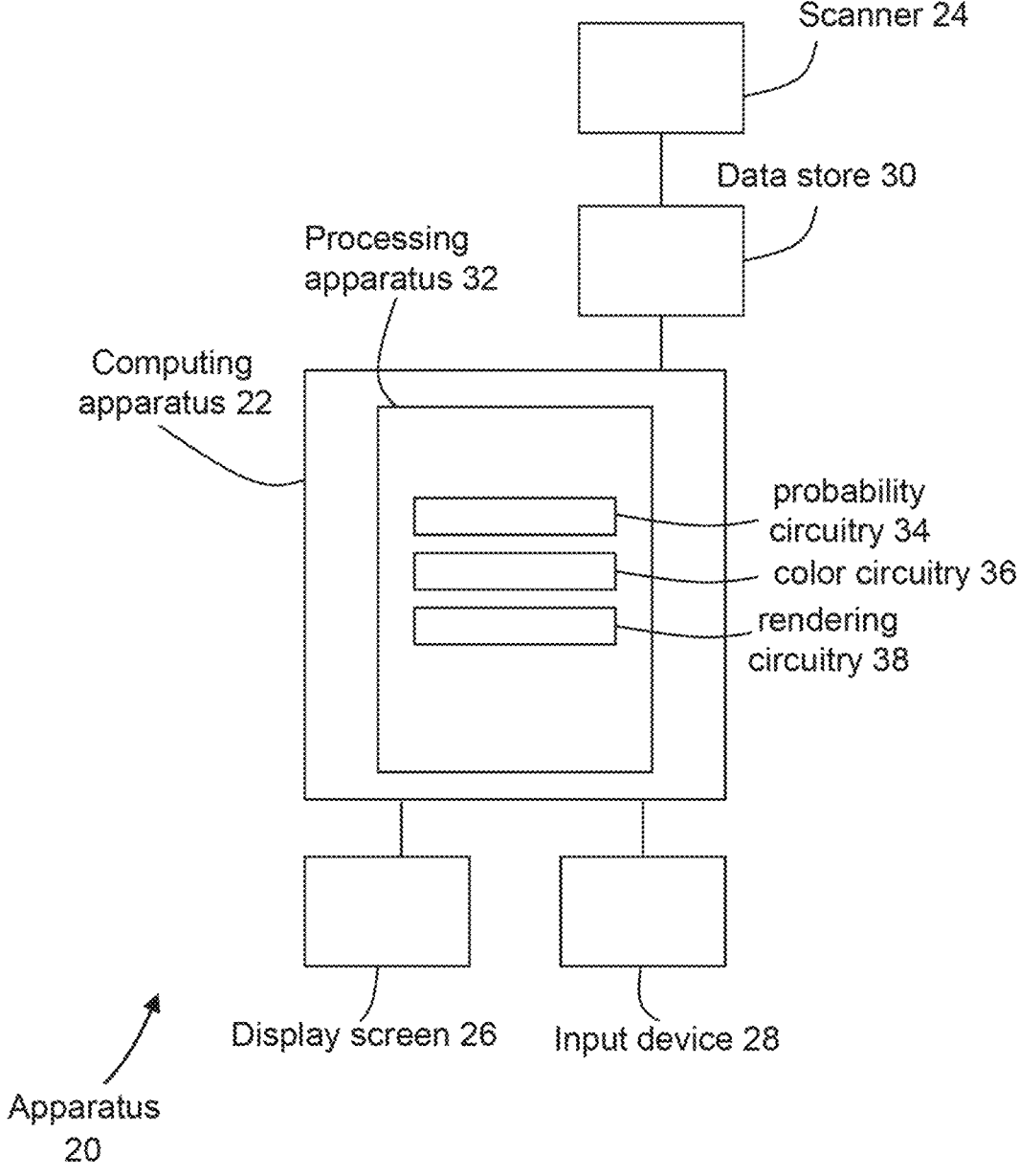
FIG. 2 is a schematic diagram of an apparatus according to an embodiment.

A medical image processing apparatus 20 according to an embodiment is illustrated schematically in FIG. 2.

The medical image processing apparatus 20 comprises a computing apparatus 22, in this case a personal computer (PC) or workstation, which is connected to a scanner 24 via a data store 30.

The medical image processing apparatus 20 further comprises one or more display screens 26 and an input device or devices 28, such as a computer keyboard, mouse or trackball.

In the present embodiment, the scanner 24 is a photon counting computed tomography (PCCT) scanner which is configured to obtain CT image data in a plurality of different wavelength channels, for example in 6 different wavelength channels. The scanner 24 is configured to generate image data that is representative of at least one anatomical region of a patient or other subject. The image data comprises plurality of radiation image data sets each representative of the same set of voxels. Each radiation image data set is representative of a respective channel and includes a data value for each voxel in said channel. In other embodiments, a single radiation image data set may include data for a plurality of channels. For example, channels may be interleaved, with all channels stored as a single volume of multi-component voxels.

In other embodiments, the scanner 24 may be a dual-energy or multi-energy CT scanner which is configured to obtain CT image data using two or more different energies.

In further embodiments, the scanner 24 may be any scanner that is configured to obtain multi-dimensional image data, for example 2D, 3D or 4D image data that is representative of different wavelengths, energies, spectral quantities, sequences or other parameters. For example, the scanner 24 may comprise a magnetic resonance (MR) scanner, computed tomography (CT) scanner, cone-beam CT scanner, positron emission tomography (PET) scanner, X-ray scanner, ultrasound scanner or multispectral optoacoustic tomography scanner. The scanner 24 may acquire data using any multi-spectral imaging modality.

In some embodiments, the scanner is an MR scanner which acquires a plurality of channels of data, each corresponding to a respective MR sequence. For example, acquisition of T1, T2 and FLAIR (fluid-attenuated inversion recovery) data may be treated as a 3D component sequence if the acquisitions are performed in the same planes.

In the present embodiment, radiation image data sets obtained by the scanner 24 are stored in data store 30 and subsequently provided to computing apparatus 22. In an alternative embodiment, radiation image data sets are supplied from a remote data store (not shown). The data store 30 or remote data store may comprise any suitable form of memory storage. In some embodiments, the medical image processing apparatus 20 is not coupled to any scanner.

Computing apparatus 22 comprises a processing apparatus 32 for processing of data. The processing apparatus 32 comprises a central processing unit (CPU) and Graphical Processing Unit (GPU). The processing apparatus 32 provides a processing resource for automatically or semi-automatically processing medical image data sets. In other embodiments, the data to be processed may comprise any image data, which may not be medical image data.

The processing apparatus 32 includes probability circuitry 34 configured to determine material probabilities using multi-dimensional image data; color circuitry 36 configured to obtain color values from determined probabilities; and rendering circuitry 38 configured to use the color values to produce a rendered image.

In the present embodiment, the circuitries 34, 36, 38 are each implemented in the CPU and/or GPU by means of a computer program having computer-readable instructions that are executable to perform the method of the embodiment. In other embodiments, the circuitries may be implemented as one or more ASICs (application specific integrated circuits) or FPGAs (field programmable gate arrays).

The computing apparatus 22 also includes a hard drive and other components of a PC including RAM, ROM, a data bus, an operating system including various device drivers, and hardware devices including a graphics card. Such components are not shown in FIG. 2 for clarity.

Figure 3:
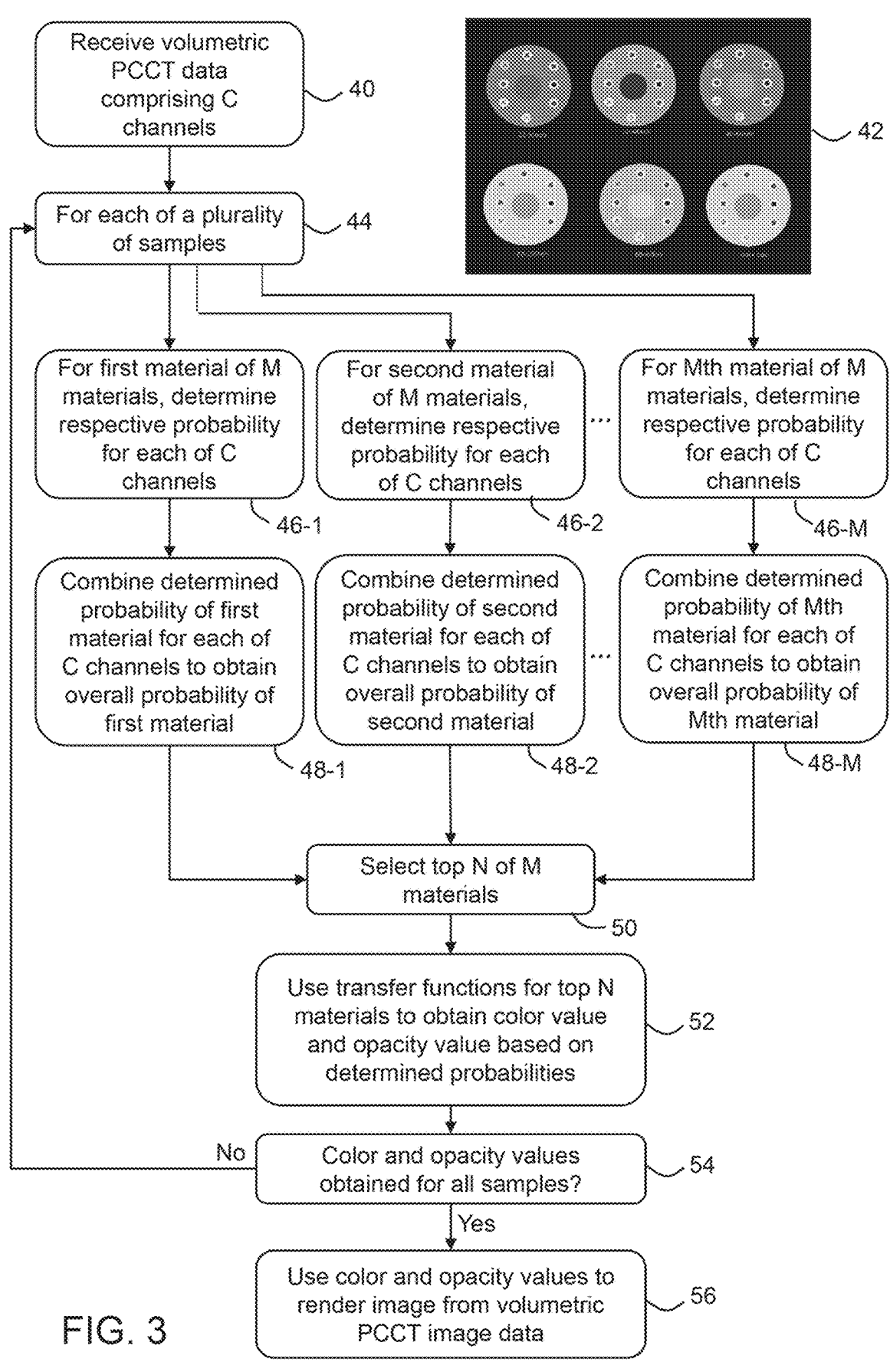
FIG. 3 is a flow chart illustrating in overview a method of an embodiment.

FIG. 3 is a flowchart illustrating in overview the method of an embodiment. In the embodiment of FIG. 3, volume rendering of multi-dimensional photon counting CT data is performed. Instead of mapping from data to a color, a scalar per-material probability metric is defined. The probability metric is then used to define a linear color mapping in probability space.

At stage 40, the probability circuitry 34 receives volumetric image data that is representative of an anatomical region of a patient or other subject.

In the present embodiment, the volumetric image data set comprises PCCT data. In other embodiments, the volumetric image data set may comprise dual-energy or multi-energy CT data. In further embodiments, the probability circuitry 34 may receive any suitable 2D or 3D image data which is representative of a plurality of channels.

The volumetric image data is representative of a plurality of voxels. With each voxel is associated respective intensity values for a plurality of channels. In other embodiments, the image data received at stage 40 may be representative of a plurality of pixels.

Each of the channels is representative of a different range of wavelengths and therefore a different range of energies of photons received. The channels may also be referred to as energy buckets or bins. The number of channels may be indicated as C. In the present embodiment, the volumetric image data comprises C radiation image data sets, one for each channel, where all of the radiation image data sets are representative of the same anatomical region of the same subject. All of the radiation image data sets are representative of the same object, where the object may comprise any anatomical feature or other feature included in the volume that is imaged.

In other embodiments, a single radiation image data set may include data for all of the channels. For example, data for different channels may be interleaved in a similar manner to a common storage format for color images.

In further embodiments, any suitable number of channels may be used to represent any suitable energy bins, spectral quantities, sequences or other parameters in any suitable modality or modalities.

In an example 42 that is shown in FIG. 3, 6 channels are used, C=6. A first channel is representative of photons having energies between 25 and 30 keV, a second channel is representative of photons between 30 and 40 keV, a third channel is representative of photons between 40 and 50 keV, a fourth channel is representative of photons between 50 and 60 keV, a fifth channel is representative of photons between 60 and 80 keV, and a sixth channel is representative of photons with energies over 80 keV. Image 42 of FIG. 3 shows the result of imaging a phantom in each of the 6 different channels. It may be seen that materials of the phantom have different greyscale values at different energies, which indicates a different degree of absorption at each of the different energies.

At stage 44 of FIG. 3, the probability circuitry 34 selects a sample at a sample position in a volume represented by the volumetric image data. In the present embodiment, the rendering to be performed on the volumetric image data comprises ray-casting, and samples are selected at positions along a pixel ray in a pixel ray front-to-back order. In other embodiments, samples may be selected in any appropriate order. The selected sample has an associated spatial position within the volumetric image data, which is representative of a corresponding spatial position in the patient or other subject.

The flow chart then proceeds to stages 46-1, 46-2 . . . 46-M and 48-1, 48-2 . . . 48-M in which the probability circuitry 34 determines a respective probability of existence of each of a plurality of materials at the selected sample position. For example, the materials may include one or more of blood, bone, air, water, muscle, skin, fat, soft tissue. The number of materials for which probabilities are determined may be represented by the letter M. The calculation of probabilities for five materials is described as an example below, but in other embodiments probabilities may be calculated for any suitable number of materials, for example 2, 3, 4, 5 or 6 materials.

At stage 46-1, the probability circuitry 34 determines probabilities that the first material is present at the selected position. The probability circuitry 34 determines a respective probability value for each channel of the C channels in the volumetric image data, where the probability value is a scalar value between 0 and 1. For example, if the volumetric image data comprises 6 channels, the probability circuitry 34 determines a respective probability value for each of the 6 channels.

In the embodiment of FIG. 3, predetermined probability curves 61, 62, 63, 64, 65, 66 are stored in the data store 30 or in any suitable data store. For example, the probability curves 61, 62, 63, 64, 65, 66 may be stored as a table or as a function. The probability curves may also be referred to as probability functions or per-channel probability functions.

Each of the probability curves 61, 62, 63, 64, 65, 66 maps intensity values to probability values. The probability curves 61, 62, 63, 64, 65, 66 may be determined using a known probability distribution for photons in each of the channels. Each of the probability curves 61, 62, 63, 64, 65, 66 defines a probability of material X for a given intensity in a given channel.

In other embodiments, probability curves may be defined or adjusted in response to a user input provided by a user. In some embodiments, the probability curves may be defined by simply thresholding high and low intensity values. A user may provide or adjust at least one high and/or low intensity value. In other embodiments, the probability curves may have more gradual transitions between probability values.

The extent of a probability curve along the horizontal axis of intensity may be described as a window level and adjusting the minimum and/or maximum extent of the probability curve may be described as window levelling.

In some embodiments, a user provides a window level input to adjust a window level of one or more of the probability curves. The probability circuitry 34 receives the window level input and performs a corresponding window level operation on one or more of the probability curves. In some embodiments, the adjusting of the window levels of the probability curves is relative to their size in the individual channels.

In some embodiments, window levelling may be performed individually on each probability curve. In some embodiments, window levels for all of the probability curves may be performed in concert. For example, all of the window levels may be narrowed, or all of the window levels may be widened. In one embodiment, the extent of all window levels is reduced by 50%, keeping the same center values. In further embodiments, any probability functions may be used that relate probability to data value. In some embodiments, the probability functions may not be probability curves.

The probability circuitry 34 uses the predetermined probability curves 61, 62, 63, 64, 65, 66 to determine the respective probability for each of the C channels.

Figure 4:
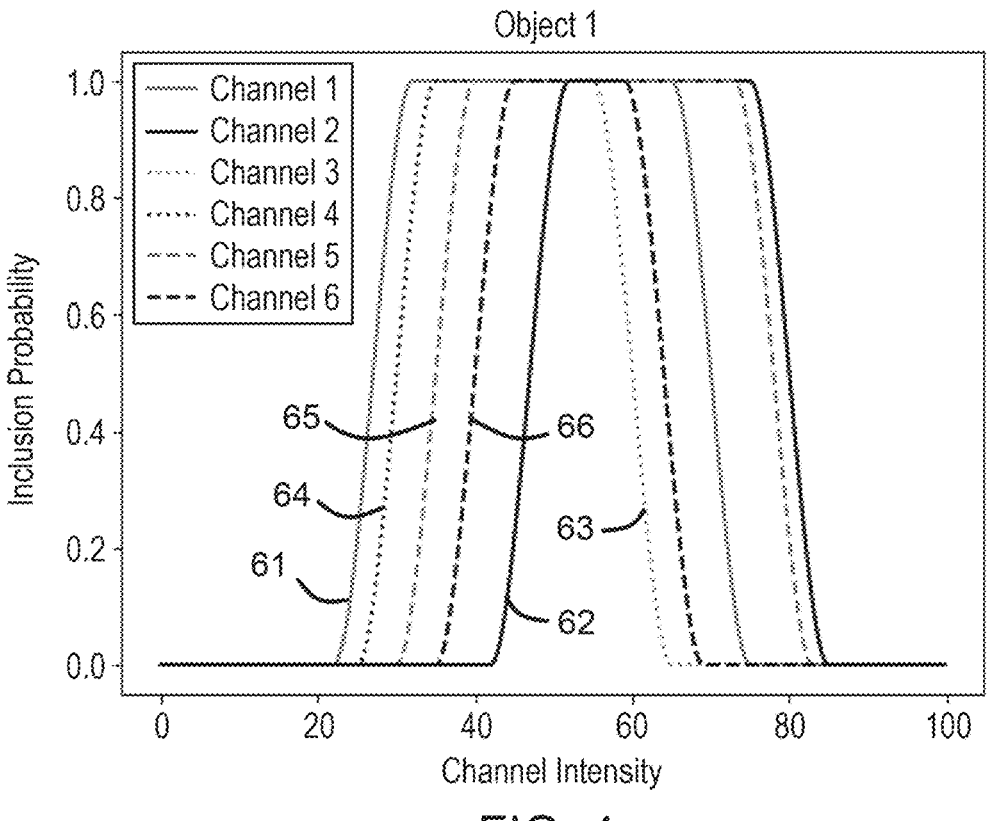
FIG. 4 is a set of channel material probability curves for a first material.

FIG. 4 is an example of a set of probability curves 61, 62, 63, 64, 65, 66 that may be used to determine whether the first material is present at the sample position. Each probability curve 61, 62, 63, 64, 65, 66 relates intensity values (for example, in Hounsfield units) in a given channel to probability values between 0 and 1. A probability value for a given channel may be obtained by identifying the intensity value for that channel and using the probability curve for that channel to obtain the probability value that corresponds to the intensity value.

All of the probability curves 61, 62, 63, 64, 65, 66 are different. This is because absorption of X-rays by a given material may typically differ at different wavelengths or energies. In other embodiments, any suitable method of determining probability values may be used and the probability values may be expressed in any suitable manner and using any suitable numerical scale.

At stage 48-1, the probability circuitry 34 combines the probability values for the C channels that were determined at stage 46-1 to obtain an overall probability value for the first material at the selected position. For example, if there are 6 channels, the probability circuitry 34 combines the 6 probability values that were determined at stage 46-1. The overall probability value is a single scalar value which is representative of the probability that the first material is present at the selected position. The overall probability value may be described as a value of a scalar per-material probability metric.

In the embodiment of FIG. 2, the probabilities for the different channels are combined by multiplying all of the probabilities for the different channels together using the equation:

$$P_{total} = \prod_{c=1}^{c=C} p_n(c, X)$$

where $p_n(c, X)$ is the probability at the selected position for an individual channel, with c being the channel and X being intensity or intensity as a function of location. $p_{total}$ is the combined probability for all channels.

In other embodiments, any suitable method of combining the probabilities from the C channels may be used.

Stage 48-1 outputs a single probability value, which is an overall probability that the selected position is representative of the first material. The single probability value for the first material is obtained by combining the respective probability values for the C channels that were determined at stage 46-1.

At stage 46-2, the probability circuitry 34 determines probabilities that a second, different material is present at the selected position using a further, different set of probability curves 71, 72, 73, 74, 75, 76. The probability circuitry 34 uses the further set of probability curves 71, 72, 73, 74, 75, 76 to determine a respective probability value for each channel of the C channels in the volumetric image data. The further set of probability curves 71, 72, 73, 74, 75, 76 may be stored in the data store 30 or in any suitable data store.

Figure 5:
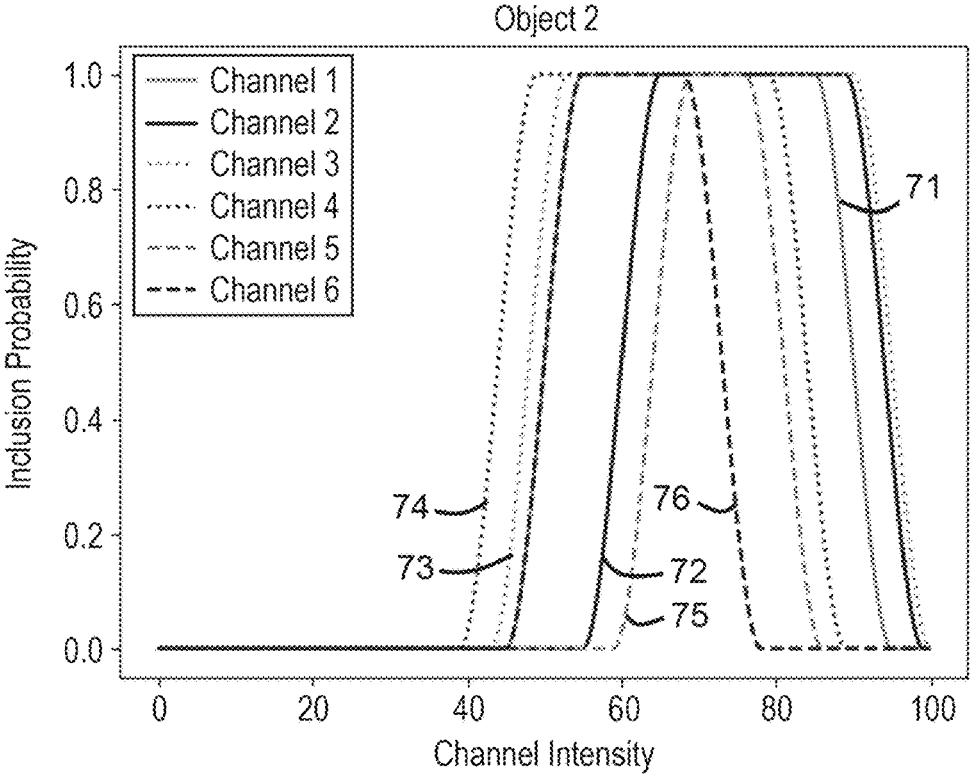
FIG. 5 is a set of channel material probability curves for a second material.

FIG. 5 is an example of a further set of probability curves 71, 72, 73, 74, 75, 76, which the probability circuitry 34 uses to determine probabilities for the second material. Each of the probability curves 71, 72, 73, 74, 75, 76 maps intensity to probability.

The further set of probability curves for the second material as shown in FIG. 5 are different from the set of probability curves for the first material as shown in FIG. 4, because they relate to different materials which have different absorption of X-rays.

Although only two sets of probability curves are illustrated herein as FIG. 4 and FIG. 5, in practice the data store 30 or any suitable data store may store as many sets of probability curves as there are materials for which probabilities are to be determined, i.e. M sets of probability curves.

At stage 48-2, the probability circuitry 34 combines the probability values for the C channels that were determined at stage 48-2 to obtain an overall probability value for the second material, for example by using the same equation that was described above with reference to the first material. Stage 48-2 outputs a single probability value, which is an overall probability that the selected position is representative of the second material. The single probability value for the second material is obtained by combining the respective probability values for the C channels that were determined at stage 48-1.

The probability circuitry 34 performs a determination of per-channel probability values similar to that described above with reference to stages 46-1 and 46-2 for each material up to material M. For example, if M is 5, the probability circuitry 34 performs stages 46-1, 46-2, 46-3 (not shown in FIG. 3), 46-4 (not shown in FIG. 3) and 46-M which may also be written as 46-5.

The probability circuitry 34 combines the per-channel probability values into a single overall probability for each of the materials up to material M, which in the embodiment of FIG. 3 uses a multiplication as described above with reference to stages 48-1 and 48-2. For example, if M is 5, the probability circuitry 34 performs stages 48-1, 48-2, 48-3 (not shown in FIG. 3), 48-4 (not shown in FIG. 3) and 48-M which may also be written as 48-5. Overall probability may be described as a scalar per-material probability metric.

The determining of per-channel probability values for material M is shown as stage 46-M in FIG. 3 and the combining into a single overall probability for material M is shown as stage 48-M in FIG. 3. Stage 48-M outputs an overall probability that the sample position is representative of the Mth material.

In other embodiments, any suitable value of M may be used.

At stage 50, the probability circuitry 34 compares the probability values for the different materials that were output at stages 48-1, 48-2 . . . 48-M. The probability circuitry 34 selects the N materials having the highest probability values, where N is a predetermined number of materials.

In some embodiments, the number of materials N to be selected may be the same as the number of materials M for which probabilities were calculated. In such embodiments, stage 50 may be omitted.

In the embodiment of FIG. 3, N=2. The probability circuitry 34 selects the 2 highest probability values from those output at stages 48-1, 48-2 . . . 48-M. The two materials selected are those having the highest probability value and the next-highest probability value.

At stage 52, the color circuitry 36 uses predetermined probability transfer functions 80, 90 for the top N materials to obtain a color value and opacity value for the selected sample based on determined probabilities.

A respective probability transfer function 80, 90 for each of the M materials is stored in the data store 30 or in any suitable data store. Each probability transfer function 80, 90 maps overall material probability to optical properties. In the embodiment of FIG. 3, the optical properties are color and opacity. Each probability transfer function 80, 90 may be used to obtain a respective color value for each possible probability value, for example each possible probability value between 0 and 1. In some embodiments, the probability transfer functions 80, 90 may be generated or altered by a user.

In the embodiment of FIG. 3, each probability transfer function provides a linear color mapping in probability space. In other embodiments, any suitable method of classifying probability into one or more optical properties may be used.

It is noted that the probability transfer functions 80, 90 of stage 52 are different from the transfer functions used in conventional volume rendering in that the transfer functions relate optical properties to probability instead of relating optical properties to intensity.

In the embodiment of FIG. 3, N=2, so the color circuitry 36 uses the probability transfer functions 80, 90 for the highest-probability and next-highest probability material.

The color circuitry 36 uses the probability transfer function 80 for the highest-probability material to convert the probability value obtained for the highest-probability material into a color value and an opacity value.

Figure 6:
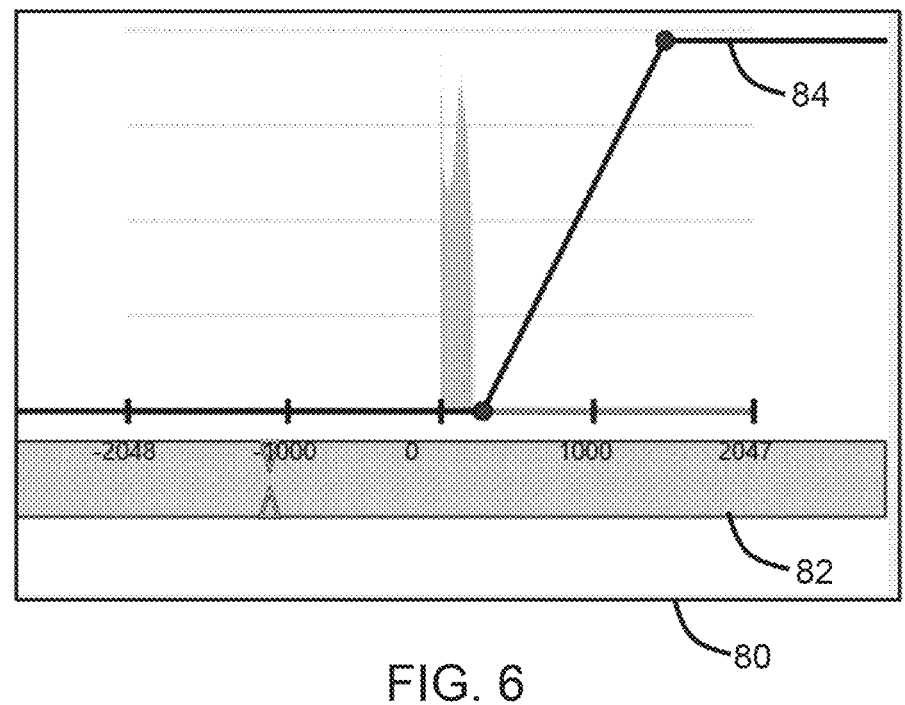
FIG. 6 is a transfer function relating color and opacity to probability for the first material.

FIG. 6 illustrates an example of a probability transfer function 80 which relates color and opacity to probability for a first material. Color is represented as bar 82. In the example of FIG. 6, the same color is used for all probability values. Opacity is plotted as line 84. In the example of FIG. 6, probability is expressed as values between 0 and 2047, where 0 is zero probability and 2047 is 100% probability. Opacity is 0 at a probability of 0 and then increases to a maximum value.

The color circuitry 36 uses the probability transfer function for the next-highest-probability material to convert the probability value obtained for the next-highest-probability material into a color value and an opacity value.

Figure 7:
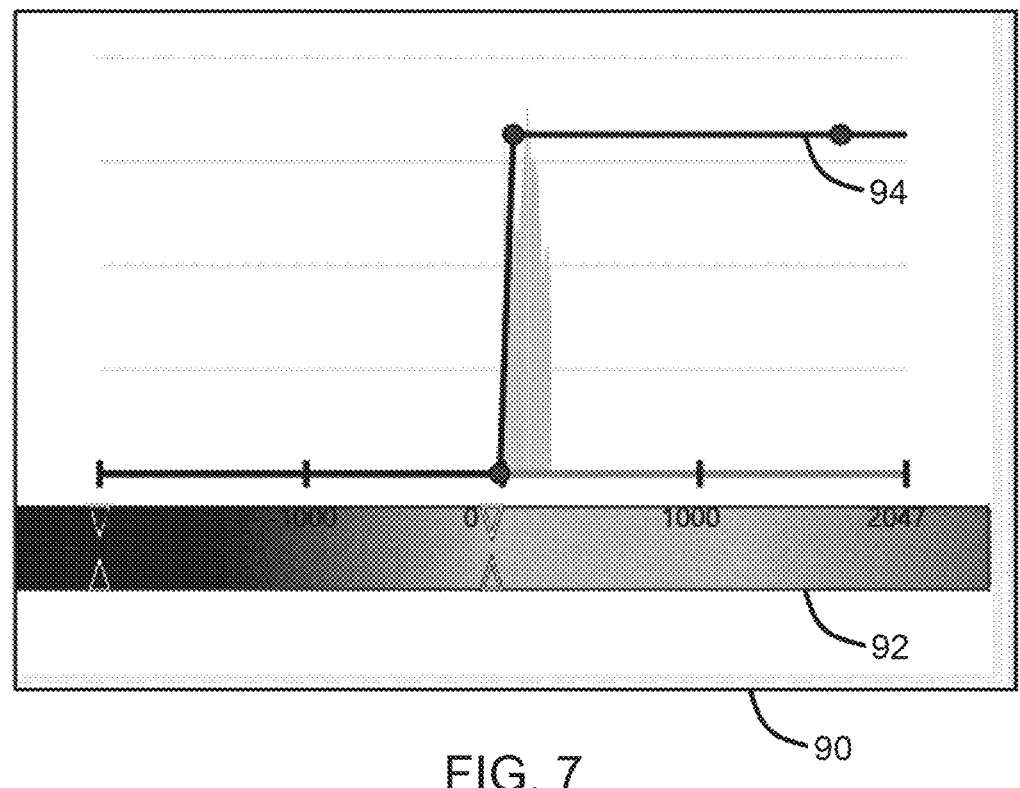
FIG. 7 is a transfer function relating color and opacity to probability for the second material.

FIG. 7 illustrates an example of a probability transfer function 90 which relates color and opacity to probability for a second, different material. Color is represented as bar 92. In the example of FIG. 7, the color that is used varies with probability value. Opacity is plotted as line 94. In the example of FIG. 7, probability is expressed as values between 0 and 2047, where 0 is zero probability and 2047 is 100% probability. Opacity is 0 at a probability of 0 and then increases to a maximum value, where the increase in opacity takes place at lower values of probability than in the transfer function of FIG. 6.

The color circuitry 36 merges the color and opacity obtained for the highest-probability material with the color and opacity obtained for the next-highest-probability material to obtain a combined color and opacity for the selected sample. Any suitable method of combining the colors and opacities may be used. For example the color and opacity values may be combined using the under operator, so that the value for the next-highest-probability material is under the value for the highest-probability material. A further method of combining colors and opacities is described below with reference to FIG. 9.

Turning back to FIG. 3, once a combined color and opacity for the selected sample have been obtained at stage 52, the method proceeds to stage 54. At stage 54, the color circuitry 36 determines whether color and opacity values have been determined for all samples. If there are samples for which no color and opacity has yet been determined, the method of FIG. 3 returns to stage 44 at which a further sample is selected. Stages 44 to 52 are repeated until a respective color and opacity have been determined for every sample that is to be used in rendering.

In the embodiment of FIG. 3, intensities for each sample are obtained by interpolation from neighboring voxels, and the interpolated intensities are converted into probabilities using probability transfer functions. In other embodiments, probability values may be calculated for each voxel or pixel in the volumetric data set.

If at stage 54 it is determined that color and opacity values have been obtained for all samples, the method of FIG. 3 proceeds to stage 56.

Figure 8:
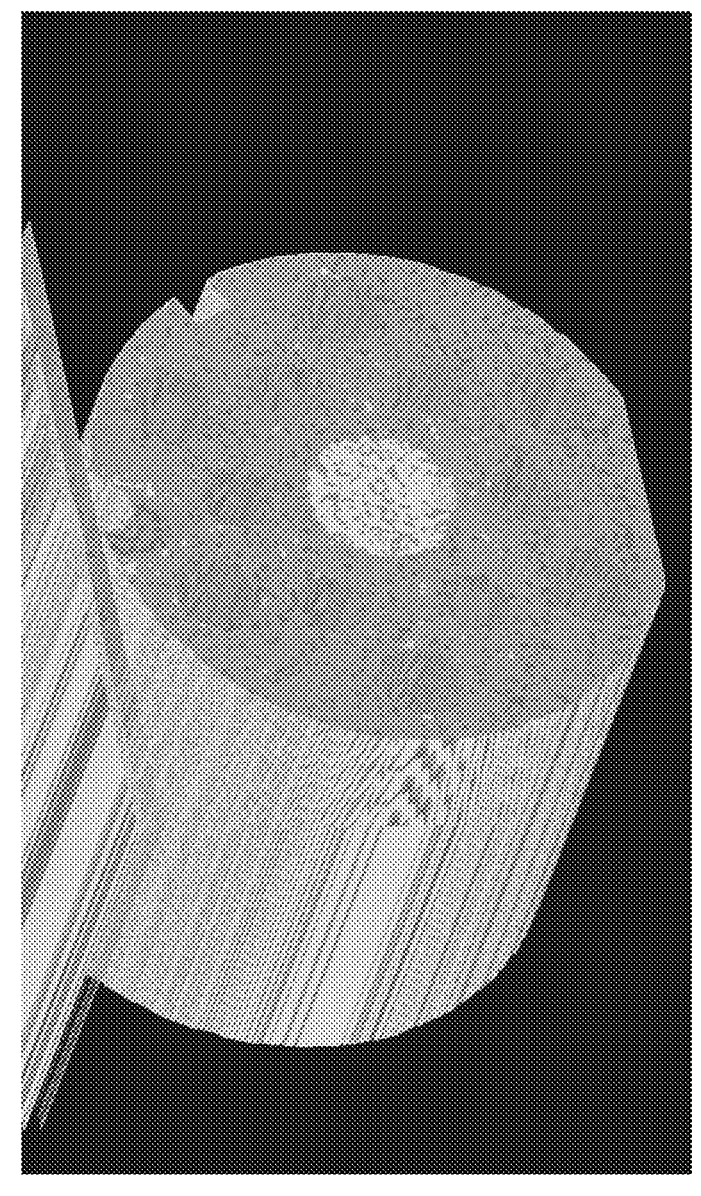
FIG. 8 is an example of an image rendered using a method of an embodiment.

At stage 56, the rendering circuitry 38 uses the color and opacity values that have been determined to render an image from the volumetric image data. Any suitable method of rendering may be used, for example shaded volume rendering using the shaded volume rendering lighting equation. FIG. 8 illustrates an example image of a phantom that is obtained using the method of FIG. 3.

The method of FIG. 3 provides a volume rendering scheme for multi-dimensional photon counting CT data. Instead of mapping from the data to a color, a scalar per-material probability metric is defined. The probability metric is then used to define a linear color mapping in probability space.

Instead of mapping optical properties to intensities, optical properties are mapped to material probabilities. Each material has a probability distribution for each CT channel which is used to define a probability value for each given intensity value. These probabilities are combined to form the probability that the sample belongs to the material.

Colors and opacities are selected based on probability values instead of being based on intensity values directly. Even though colors may blend gradually from one material to another, depending on settings, the mapping is not related to material composition. Instead, the mapping is based purely on the probability that a sample belongs to that material type.

By selecting colors based on probability of materials, a rendering of a multi-channel volume may be made easier to interpret than if the colors were to be based on intensities from all of the channels. Probability transfer functions may be relatively simple and easy to store. It may be straightforward for a user to create or adjust a probability transfer function to result in a desired visual effect.

In some embodiments, color, opacity, or both color and opacity may be used to represent probability. In further embodiments, any suitable optical property may be used to represent probability. For example a bidirectional reflectance distribution function (BRDF) parameter such as specular amount or exponent may be used to represent probability. A global illumination (GI) parameter may be used to represent probability, for example, an advanced GI parameter such as phase function scattering coefficient.

In the embodiment of FIG. 3, N=2 and the top 2 materials are selected at stage 50 of FIG. 3. In other embodiments, more than two top materials may be used at stage 50 and the colors combined for all of the top materials. For example, N may be 3 or 4. However, if more than two materials are used, there may be more colors to merge at stage 50, and it may be the case that merging too many colors may result in dull colors. Therefore, in some circumstances, it may be considered optimal to use two materials at stage 50, N=2, even if the number of materials M is more than two.

In the embodiment of FIG. 3, the top 2 materials are determined on a per-sample basis. The top 2 materials for one sample position may be different from the top 2 materials for a different sample position. In other embodiments, a top N materials may be selected based on the probability values for a region of the volumetric data, or for the volumetric data as a whole. For example a top 2 materials may be selected for rendering and probability values for those top 2 material may be used in the rendering of every sample.

In some embodiments, the total probability of the first two materials is normalized to total 100%. For example, for one sample, the probabilities may be 55% for a first material and 45% for a second material. For a different sample, the probabilities may be 36% for material 1 and 74% for material 2.

Figure 9:
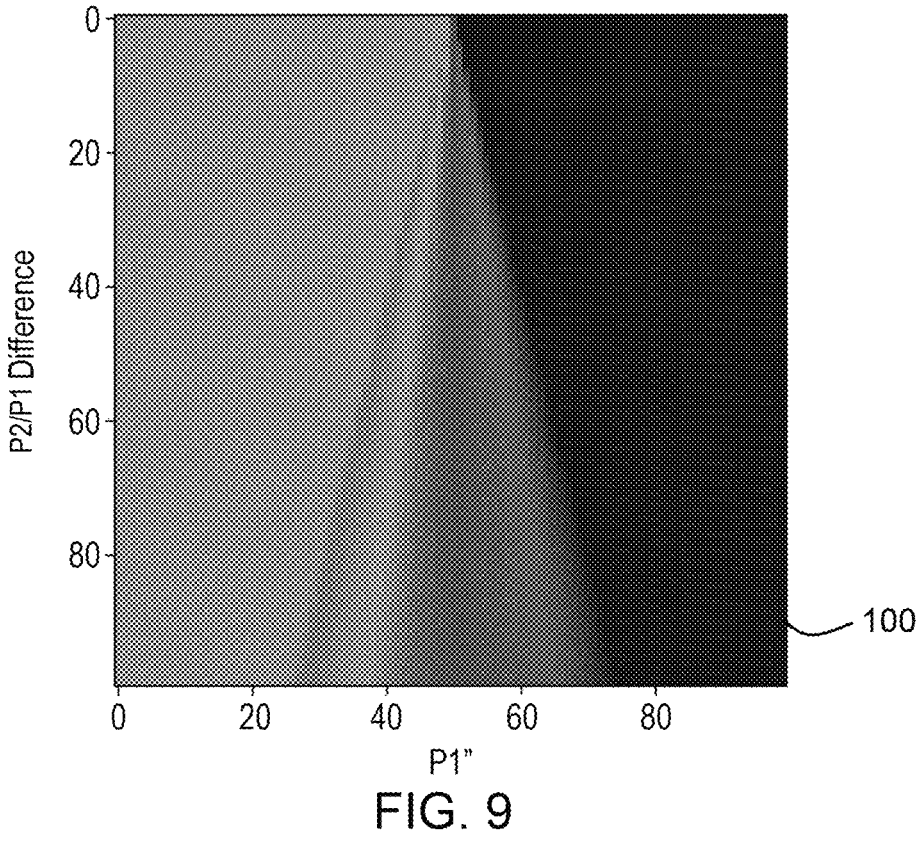
FIG. 9 is an custom 2-dimensional color table.

FIG. 9 shows an example of a color table 100 that may be used to perform a method of combining probabilities for the top two materials in accordance with a further embodiment. The color table 100 may also be described as a pair-wise color transition table.

The probabilities for the top two materials are designated P1 and P2 respectively. A normalized probability value Pn" is introduced which is Pn/(P1+P2), where n is 1 or 2. In this adjusted space, P1"=1−P2" and P2"=1−P1" since the normalized probabilities are constructed such that they sum to 1.

It is noted that in some scenarios, the probability for the highest-probability material may be very high, for example 95%, whereas in other scenarios the probability for the highest-probability material may be 50% or less. It is also noted that there in some scenarios, the two highest-probability materials may be very close in probability, whereas in other scenarios, the two highest-probability materials may differ significantly in probability. If the highest-probability material has a much higher probability than the next-highest-probability material, a prediction that the sample corresponds to the highest-probability may have high confidence. If the highest-probability material only has a slightly higher probability than the next-highest-probability material, a prediction that the sample corresponds to the highest-probability may have less confidence.

The color table 100 is designed to result in sharp transitions in color between materials where predictions may be made with high confidence, and more extended transitions in color between materials where predictions are made with lower confidence.

In the embodiment of FIG. 9, the color table 100 is a two-dimensional color table. The color table 100 may be stored in the data store 30 or any suitable data store. The color table 100 may be stored as, for example, a look-up table or a function. In other embodiments, any suitable function may be used to relate two dimensions of probability to color.

A horizontal axis of the color table 100 is representative of a normalized probability P1" of the first material. As stated above, the normalized probability P1" of the first material and the normalized probability P2" of the second material are related in that P2"=1−P1". Therefore the horizontal axis that represents P1" also represents 1−P2".

A vertical axis of the color table 100 is representative of a non-normalized probability P2 of the second material, or a difference in probability between the top two materials, P2 and P1

In FIG. 9, each probability is represented on a scale from 0 to 100% probability.

At the top of the color table 100, P2 is low or the difference P2–P1 is low. At the bottom of the color table, P2 is high or the difference between P2 and P1 is high.

Where P1 is high or the difference between P1 and P2 is high, it may be considered that the material may be determined at high confidence and so a sharp color transition between materials is used. Where P1 is low or the difference between P1 and P2 is low, a more gradual color transition between materials is used.

In some embodiments, multiple color tables 100 are used and are stored in data store or in any suitable data store. Each color relates to a different pair of top materials.

The use of a two-dimensional color table 100 may allow custom transitions by having a 2D table per pair of objects. Confidence may be represented in addition to material type. By using a pair-wise color transition table and normalizing probabilities, a custom color transition may be selected based on an overall confidence level for material selection.

In the embodiment in which the color table 100 is used, the color circuitry 36 at stage 52 selects a color for the sample from the color table using values for P1" and P1 or P1–P2.

Figure 10:
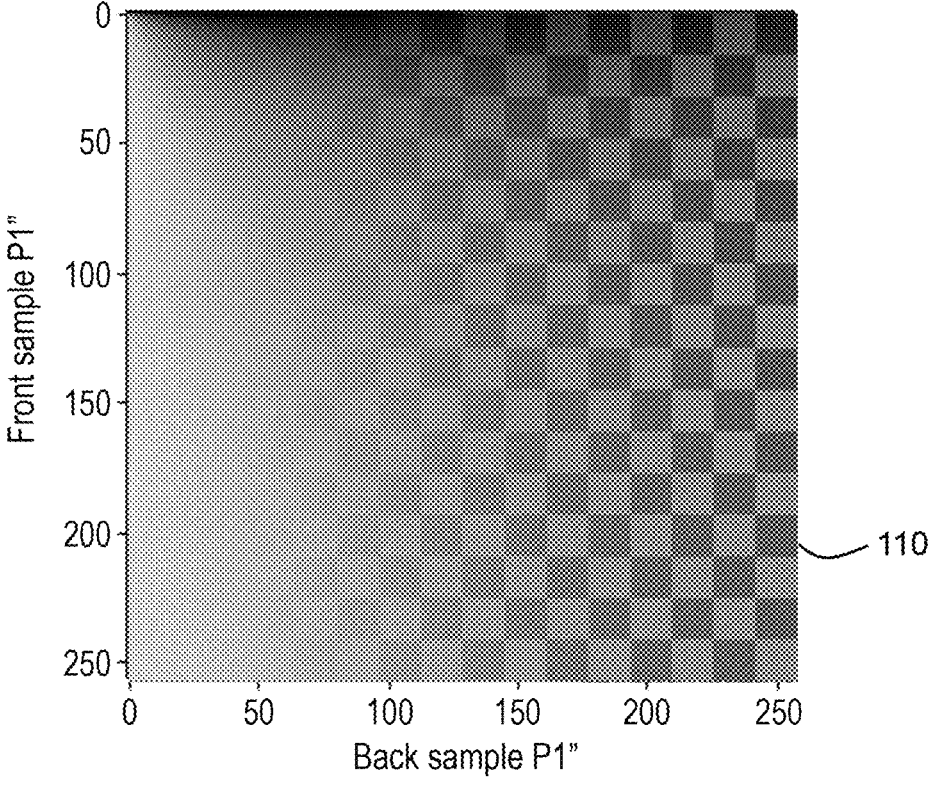
FIG. 10 is a plot of pre-integrated color values.

FIG. 10 shows an example of use of normalized probability values to achieve pre-integration.

Pre-integration is a technique that involves using colors that are pre-computed for each interval between samples. In typical two-dimensional (2D) pre-integration, opacity and color values for each possible pair of intensity values and sample spacings are pre-computed using a transfer function and stored in a look-up table. In the method of FIG. 10, two-dimensional pre-integration is instead performed using probability values.

The embodiment of FIG. 10 again uses the normalized Pn"=Pn/(P1+P2). In the adjusted space of normalized probability values, P1"=1–P2" and P2"=1–P1". A smoothly varying probability field is assumed. Once colors for P1" are obtained, colors for P2" are implied. Pre-integration is performed between P1", P2" pairs defining a linear transition in between.

A pre-integration table 110 is stored in the data store 30 or in any suitable data store. The pre-integration table 110 has been pre-calculated. The pre-integration table relates color and opacity to normalized probability values P1", P2" for a front sample and a back sample. In other embodiments, any suitable pre-integration function may be stored which related P1" and/or P2" values to color and opacity for pairs of front and back samples.

In the pre-integration table 110 illustrated in FIG. 10, back sample P1" is represented on the horizontal axis and front sample P1" is represented on the vertical axis. The pre-integration table 110 is the result of determining a respective color and opacity contribution that results from each possible combination of back sample P1" and front sample P2". The pre-integration table is shown using a checkerboard background. The checkerboard is less visible in parts of the space where the contribution has greater opacity.

The pre-integration table 110 is used to perform pre-integration in rendering. Consider a back sample and a front sample obtained as part of ray-casting in volume rendering. The back sample and front sample each have respective P1" values. P2" values may be implied from the P1" values. When rendering the back sample and front sample pair, the rendering circuitry 38 accesses the pre-integration table 110 to obtain a pre-integrated color and opacity for the back sample and front sample pair.

In other embodiments, the rendering circuitry 36 may use pre-integration contributions from any suitable representation of pre-integrated contributions in the rendering of the image at stage 56.

In further embodiments, the probability values for the top N materials for each sample as compared at stage 50 may be used to form a differential of a probability field defined by the probabilities for each sample. The differential of the probability field may be considered to be a gradient of overall probability. The differential of the probability field at each sample may be used as a normal for use in rendering using the shaded volume rendering lighting equation. In other embodiments, a respective gradient may be produced for each channel using the sample probabilities and the resulting gradients may be combined, for example by multiplying the gradients for each channel. In some embodiments, gradients from each channel may be weighted by the probability for that channel. In other embodiments, any suitable manner of obtaining or combining gradients may be used.

Embodiments above are described in relation to PCCT data having multiple channels. In other embodiments, similar methods may be used to process any appropriate multi-dimensional data, for example data obtained by dual-energy or multi-energy CT or any multi-spectral imaging modality, for example multispectral optoacoustic tomography. In some embodiments, the different dimensions of data are different sequences in multi-sequence MR, for example T1, T2 and FLAIR sequences.

Certain embodiments provide a medical image processing apparatus comprising processing circuitry configured to:

receive a plurality of radiation image data each corresponding to a plurality of energy bins, wherein the plurality of radiation image data images a same object, estimate, based on data values of pixels/voxels included in the plurality of radiation image data, material probabilities which indicate existence probabilities of materials in a position corresponding to a pixel/voxel of the plurality of radiation image data, specify a rendering parameter of the pixel/voxel based on the material probabilities.

The processing circuitry may be further configured to specify a transfer function related to rendering based on the material probabilities.

The processing circuitry may be further configured to specify an opacity and color value related to the pixel/voxel based on the material probabilities and the transfer function.

Certain embodiments provide a volume rendering method comprising:

Multi-dimensional imaging data of dimension C;

A set of materials each with:

C functions defining the probability that the voxel corresponds to the material given the channel intensity A transfer function that maps from overall probability to a color/opacity in which the classification is done by combining probabilities of each material and each channel until an overall material probability ranking can be established for the sample. The top N materials are then transferred into colors and combined to a single color which becomes part of the volume rendering integral.

The probabilities for the top N materials may be further evaluated to form the differential of the probability field for use as a normal in the shaded volume rendering lighting equation.

It may be that N=2 and a custom pair-wise color transition table is used to transfer the colors. The probabilities may be normalized so that we can select a custom color transition based on the overall confidence of the material selection.

The same normalization may allow us to define a pre-integration function between the front/back color pairs.

Window level user operation may be carried out on the probability curves relative to their size in the individual channels.

Certain embodiments provide an image rendering system comprising a processing resource configured to: obtain multi-dimensional imaging data that comprises, for each location in a volume, N channels of data; access, for each material of a set of possible materials, functions representing a probability that the material is present given values for the N channels of data; determine for each voxel or other location the probability of one or more of the materials being present, based on the values for the N channels of data for that voxel or other location and the functions; for each voxel or other location, apply at least one transfer function that maps from probability to color and/or opacity thereby to determine color and/or opacity; and render an image using the determined colors and/or opacities.

The determining of probabilities may comprise combining probabilities of each material and each channel until an overall material probability ranking is established for each voxel or other location, and the applying of the transfer function comprises applying transfer functions for the P (where P is an integer) most probable materials for each voxel or other location and combining the resulting colors and/or opacities to obtain a respective color and/or opacity for each voxel or other location.

The materials may comprise one or more of blood, bone, air, water, muscle, skin, fat, flesh.

The processing resource may be configured to process the probabilities for the P most probable materials to obtain a differential of a probability field for use as a normal in a shaded volume rendering lighting equation.

It may be that P=2, a pair-wise color transition table is used to obtain the colors and/or opacities, and the processing resource is configured to normalize the probabilities thereby to enable selection of a custom color transition based on an overall confidence level for material selection.

The processing resource may be configured to use the normalized probabilities to define a pre-integration function between front/back color pairs.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image processing apparatus, comprising: processing circuitry configured to:
   receive radiation image data for each of a plurality of different channels, wherein the radiation image data for all of the plurality of different channels represents a same anatomical region of a same subject; and
   for each position of a plurality of positions represented in the radiation image data:
      estimate, based on data values for the position in each of the plurality of different channels, material probabilities which indicate a respective probability of each of a plurality of materials existing at the position; and
      specify a value for at least one rendering parameter at the position based on the material probabilities,
   wherein the processing circuitry is further configured to estimate the material probabilities by, for each material of the plurality of materials, estimating a respective per-channel probability for each of the plurality of different channels, and combining the respective per-channel probabilities to obtain the material probability for said material.

2. The medical image processing apparatus according to claim 1, wherein the processing circuitry is further configured to render an image using, for each position of the plurality of positions, the specified value for the at least one rendering parameter.

3. The medical image processing apparatus according to claim 1, wherein the plurality of different channels are representative of different energy bins.

4. The medical image processing apparatus according to claim 3, wherein the processing circuitry is further configured to receive the radiation image data, which is acquired using photon-counting CT (PCCT), dual-energy CT, or multi-energy CT, and
   each of the energy bins corresponds to a respective energy channel of a PCCT, dual-energy CT, or multi-energy CT acquisition.

5. The medical image processing apparatus according to claim 1, wherein the processing circuitry is further configured to specify at least one function that relates values for the at least one rendering parameter to material probability values.

6. The medical image processing apparatus according to claim 5, wherein the at least one function that relates values for the at least one rendering parameter to material probability values comprises at least one probability transfer function.

7. The medical image processing apparatus according to claim 6, wherein the processing circuitry is further configured to specify the value for the at least one rendering parameter using the at least one probability transfer function and the estimated material probabilities.

8. The medical image processing apparatus according to claim 7, wherein the processing circuitry is further configured to specify the value for the at least one rendering parameter using the at least one probability transfer function and the estimated material probabilities by specifying an opacity value and a color value for the position.

9. The medical image processing apparatus according to claim 1, wherein the processing circuitry is further configured to combine the respective per-channel probabilities by multiplying together the respective per-channel probabilities.

10. The medical image processing apparatus according to claim 1, wherein the processing circuitry is further configured to estimate the respective per-channel probability for each of the plurality of different channels by using a set of per-channel probability functions that each relate probability to data value.

11. The medical image processing apparatus according to claim 10, wherein the processing circuitry is further configured to receive a user input from a user, and determine or adjust at least one of the per-channel probability functions in dependence on the received user input.

12. The medical image processing apparatus according to claim 10, wherein the processing circuitry is further configured to receive a window level input from a user, and perform a window level operation on one or more of the per-channel probability functions in response to the received window level input.

13. The medical image processing apparatus according to claim 1, wherein the processing circuitry is further configured to specify the value for the at least one rendering parameter by selecting N materials of the plurality of materials having the highest estimated material probabilities and using the material probabilities for said N materials to specify the value for the at least one rendering parameter, wherein N is an integer greater than or equal to one.

14. The medical image processing apparatus according to claim 1, wherein the processing circuitry is further configured to normalize at least some of the material probabilities.

15. The medical image processing apparatus according to claim 14, wherein the processing circuitry is further configured to use the normalized probabilities to perform pre-integration of front and back samples.

16. The medical image processing apparatus according to claim 1, wherein the processing circuitry is further configured to select N materials of the plurality of materials having the highest estimated material probabilities, and to use the material probabilities for said N materials to obtain a differential of a probability field for use as a normal, wherein N is an integer greater than or equal to one.

17. The medical image processing apparatus according to claim 1, wherein the plurality of materials comprises one or more of blood, bone, air, water, muscle, skin, fat, or soft tissue.

18. A medical image processing apparatus, comprising:
    processing circuitry configured to:
        receive radiation image data for each of a plurality of different channels, wherein the radiation image data for all of the plurality of different channels represents a same anatomical region of a same subject; and
    for each position of a plurality of positions represented in the radiation image data:
        estimate, based on data values for the position in each of the plurality of different channels, material probabilities which indicate a respective probability of each of a plurality of materials existing at the position; and
        specify a value for at least one rendering parameter at the position based on the material probabilities,
    wherein the processing circuitry is further configured to normalize at least some of the material probabilities, and
    wherein the processing circuitry is further configured to specify the value for the at least one rendering parameter by selecting two materials of the plurality of materials having the highest estimated material probabilities, and using normalized probabilities for said two materials and a pair-wise color transition function to obtain the value for the at least one rendering parameter.

19. A medical image processing method, comprising:
    receiving radiation image data for each of a plurality of different channels, wherein the radiation image data for all of the plurality of different channels represents a same anatomical region of a same subject; and,
    for each position of a plurality of positions represented in the radiation image data:
        estimating, based on data values for the position in each of the plurality of different channels, material probabilities which indicate a respective probability of each of a plurality of materials existing at the position; and
        specifying a value for at least one rendering parameter at the position based on the material probabilities,
    wherein the estimating step further comprises estimating the material probabilities by, for each material of the plurality of materials, estimating a respective per-channel probability for each of the plurality of different channels, and combining the respective per-channel probabilities to obtain the material probability for said material.

* * * * *